United States Patent [19]
Rosenblatt et al.

[11] Patent Number: 5,928,667
[45] Date of Patent: Jul. 27, 1999

[54] DRUG DELIVERY DEVICE AND METHOD FOR EMPLOYING THE SAME

[75] Inventors: Joel Rosenblatt, Palo Alto; Vivek Shenoy, Santa Clara, both of Calif.

[73] Assignee: University of Maryland, Baltimore, Md.

[21] Appl. No.: 08/755,349

[22] Filed: Nov. 25, 1996

Related U.S. Application Data

[63] Continuation of application No. 08/265,848, Jun. 24, 1994, abandoned.

[51] Int. Cl.$^6$ ............................................. A61K 9/14
[52] U.S. Cl. ..................... 424/484; 424/422; 424/488; 514/964; 514/965
[58] Field of Search ..................... 424/422, 426, 424/488, 484, 487; 514/21, 54, 56, 59, 964, 965; 523/105, 113; 530/356, 357

[56] References Cited

U.S. PATENT DOCUMENTS

| | | | |
|---|---|---|---|
| 4,164,559 | 8/1979 | Miyata et al. | |
| 4,291,013 | 9/1981 | Wahling et al. | |
| 4,347,234 | 8/1982 | Wahling et al. | |
| 4,803,075 | 2/1989 | Wallace et al. | 424/423 |
| 4,837,285 | 6/1989 | Berg et al. | 523/105 |
| 4,925,677 | 5/1990 | Feijen | 424/484 |
| 5,116,824 | 5/1992 | Miyata et al. | 514/21 |
| 5,204,382 | 4/1993 | Wallace et al. | 424/423 |
| 5,356,629 | 10/1994 | Sander et al. | 424/422 |
| 5,631,243 | 5/1997 | Kelman et al. | 514/56 |
| 5,752,974 | 5/1998 | Rhee et al. | 606/214 |

OTHER PUBLICATIONS

Singh et al, "Diffusion and Desorption Controlled Polypeptide Release from Collagen Matrices", *Proceed. Intern. Symp. Control. Rel. Bioact. Mater.,* 21 (1994).

Singh et al, "A Fundamental Study of Electrostatic Effects in the Release of Charged Polypeptides from Collagen Hydrogels", ACS Meeting (May 1994).

Rosenblatt et al, "Chain Rigidity and Disffusional Release in Biopolymers Gels", *Proceed. Intern. Symp. Control. Rel. Bioact. Mater.,* 20:264–265 (1993).

Rosenblatt, "Mesh Size Measurement in Rigid and Flexible Polyelectrolyte Matrices" *ACS Conference,* Denver, Poster (1993).

Singh et al, "Polypeptide Delivery from Collagen: Electrostatic Effects", *Proceed. Intern. Symp. Control. Rel. Bioact. Mater.,* 20 (Jul. 1993).

*Primary Examiner*—Robert H. Harrison
*Attorney, Agent, or Firm*—Sughrue, Mion, Zinn Macpeak & Seas, PLLC

[57] ABSTRACT

A drug delivery device comprising a single phase matrix of a rigid polymer and a flexible polymer, useful for sustained release of a pharmaceutically active ingredient, as well as a method for employing the same, are disclosed.

30 Claims, 7 Drawing Sheets

DRUG DELIVERY DEVICE AND METHOD FOR EMPLOYING THE SAME

This is a Continuation of application Ser. No. 08/265,848, filed Jun. 24, 1994, abandoned.

FIELD OF THE INVENTION

The present invention relates to a drug delivery device for the sustained release of pharmaceutically active ingredients. In particular, the present invention relates to a drug delivery device comprising a single phase matrix of a rigid polymer and a flexible polymer, as well as a method for employing the same.

BACKGROUND OF THE INVENTION

Diffusion of drugs enclosed in polymer matrices is important in many biomedical and biochemical applications. The term "drug" as used herein refers to any substance having pharmaceutical activity in a subject.

Following implantation of such matrices, and due to the difference in the concentration gradient of the amount of drug in the matrix relative to the amount of drug in the surrounding tissues, there is a driving force for the drug to leave the matrix by diffusion.

When the mesh size or "pore" size in a matrix, which is the distance between neighboring polymer chains in the matrix, is smaller than the size of the diffusing drug, the release rate of the drug is decreased because there is an increase in diffusion hindrance. Flexible polymers can fill space more effectively than rigid polymers when concentrated. Thus, it is usually possible to obtain much smaller mesh sizes with flexible polymers than when using rigid polymers.

However, diffusion hindrance increases in relation to increased flexibility of the polymer used in the matrix (Johansson et al, *Macromolecules*, 24: 6019 (1991)). That is, polymers which are more rigid generally reduce diffusion rates more effectively than flexible polymers having the same mesh size. The reason for this difference is thought to be that the primary resistance to diffusion in flexible polymer matrices is frictional. Flexible polymer chains can distort, and thus allow the drug to more readily diffuse out of the matrix (Phillies, *J. Phys. Chem.*, 93: 5029 (1989)). In contrast, rigid polymer chains act as immovable obstacles, and cause the diffusing drug to take a tortuous and much more restricted path in leaving the matrix (Doi et al, Chapter 9, *The Theory of Polymer Dynamics*, Clarendon Press, Oxford (1986)). However, due to the molecule's rigidity, one cannot obtain the smaller mesh sizes with a rigid polymer which can be achieved using a flexible polymer.

SUMMARY OF THE INVENTION

Accordingly, an object of the present invention is to provide a drug delivery device which allows for sustained release of pharmaceutically active ingredients.

Another object of the present invention is to provide a method for sustained release of pharmaceutically active ingredients in vivo.

These and other objects of the present invention, which will be apparent from the detailed description of the invention provided hereinafter, have been met in one embodiment by a drug delivery device comprising a single phase matrix of a rigid polymer and a flexible polymer.

DETAILED DESCRIPTION OF THE INVENTION

As discussed above, the objects of the present invention have been met, in one embodiment, by a drug delivery device comprising a single phase matrix of a rigid polymer and a flexible polymer.

It is important that both the rigid polymer and the flexible polymer have the same charge, i.e., that they are both either negatively-charged or positively-charged so that it is possible to form a single phase mixture with the combined polymers. That is, the use of either two negatively-charged polymers or two positively-charged polymers prevents phase separation, i.e., the formation of fibers or precipitate, caused by electrostatic charge repulsions between the rigid and flexible polymers.

The phrase "negatively-charged" as used in the present invention means that the polymer has a negative charge at pH 7.0. The phrase "positively-charged" as used in the present invention means that the polymer has a positive charge at pH 7.0.

The rigid polymers have a rod-like structure. In the present invention, the rigid polymers have a molecular weight of about 100 to 1,000 KDa, preferably about 300 to 600 KDa. Rigid polymers having a molecular weight below about 100 KDa are disadvantageous because they will flow to readily. Rigid polymers having a molecular weight above about 1,000 KDa are disadvantageous because the pores in the matrix will be too large.

An example of a rigid polymer which can be employed in the present invention is collagen. Collagen is a naturally-occurring structural protein with a molecular weight of approximately 300 KDa. The tightly wound triple helical structure of collagen makes it behave like an inelastic rigid rod in solution, thereby distinguishing it from most other biopolymers which are flexible (U.S. Pat. No. 4,164,559). Therefore, collagen is preferably used as the rigid polymer in the drug delivery device of the present invention.

Collagen can be negatively-charged by succinylating vitrogen following the procedure described in U.S. Pat. No. 4,164,559, which is incorporated herein by reference in its entirety. This method is a simple way to introduce a negative charge into collagen. However, reagents other than succinic anhydride can be employed to make collagen negatively-charged as well.

For example, sulfosuccinimidyl acetate or sulfosuccinimidyl-3-(4-hydroxyphenyl)propionate (Bolton-Hunter reagent) can also be employed using the procedure described in Thompson et al, *Biochem.*, 26: 743–750 (1987). These compounds make collagen negatively-charged by blocking positive groups from ionizing. Alternatively, glutaric acid can be used in place of succinic anhydride to negatively-charge collagen by following the same procedure as used in succinylating collagen. The specific process to treat the collagen is not critical to the present invention; all that is necessary is a process which can provide a negatively-charged collagen in the form of rigid-rod molecule, i.e., not denatured, at pH 7.0.

Collagen can be positively charged by methylating collagen via well known procedure. The process of making collagen positively-charged is not critical to the present invention; all that is necessary is a process which can provide a positively-charged collagen in the form of rigid-rod molecule, i.e., not denatured, at pH 7.0.

The rigid polymer used in the present invention may be in an injectable, non-crosslinked solution, or cross-linked as a membrane (or any solid form) following mixing with the negatively-charged flexible polymer. For example, a crosslinked matrix may be prepared by mixing partially succinylated collagen, a negatively-charged flexible polymer, and the drug of interest, and then adding this mixture into a glutaraldehyde bath.

In this manner, the collagen is crosslinked into a solid network and entraps the flexible polymer and the drug of interest. The specific method of crosslinking collagen is not critical to the present invention provided that the drug to be incorporated in the crosslinked matrix is non-reactive during the crosslinking process.

The negatively-charged flexible polymers are flexible coil polymers. In the present invention, the negatively-charged flexible polymers have a molecular weight of at least 100 KDa, preferably 100 KDa to 10,000 KDa, most preferably 1,000 KDa to 10,000 KDa. Flexible polymers having a molecular weight below 100 KDa are disadvantageous because they flow from the matrix too easily.

Examples of negatively-charged flexible polymers which can be employed in the present invention include hyaluronic acid (HA), polyacrylic acid (PAA), and dextran sulfate. Any glucose aminoglycan over 100 KDa can also be employed as the flexible polymer in the present invention.

Hyaluronic acid is preferably used as the negatively-charged flexible polymer in the drug delivery device of the present invention in view of biocompatability in the matrix.

A rigid polymer can be distinguished from a flexible polymer in relation to persistence length. For example, the persistence length for collagen is approximately 170 nm (Nestler et al, *Biopolymers,* 22: 1747 (1983); and Saito et al, *Biopolymers,* 21: 715 (1982)). In contrast, the persistence length for hyaluronic acid is approximately 3.7 nm (Cleveland, *Arch Biochem. Biophys.,* 180: 57 (1987)).

The persistence length for the rigid polymer should be at least 10 times the persistence length of the flexible polymer, preferably between 10 times to 100 times the persistence length of the flexible polymer.

The ratio of the rigid polymer to flexible polymer employed in the device of the present invention will vary depending on the desired release rate and handling characteristics. However, generally the weight ratio of rigid polymer to flexible polymer should be about 50–90%, preferably about 60–80%, most preferably about 75%.

The drug delivery device of the present invention can be prepared by combining a negatively-charged rigid polymer and a negatively-charged flexible polymer, or a positively-charged rigid polymer and a positively-charged flexible, in a single phase mixture, i.e., a homogeneous solution. The single phase mixture is prepared by mixing a solution of a rigid polymer with a solution of a flexible polymer by exchange between two vessels, e.g., two syringes. The drug is incorporated in the matrix by initially mixing it with the flexible polymer, or co-dissolving it with the flexible polymer.

The device of the present invention is particularly effective for sustained release of very large growth factors, such as Factor VIII, Factor IX, and Protein C. However, one skilled in the art would realize that the specific pharmaceutically active ingredients employed is not critical to the invention. Thus, additional examples of pharmaceutically active ingredients which can be employed in the matrix of the present invention include any drug larger than about 4 nm to about 30 nm. Preferably, the drug is about 5 nm to about 20 nm in size. If the drug is of an opposite charge to the matrix, it may be adsorbed and not released into the surrounding tissue. Thus, it is preferable that the drug have a similar charge as the matrix or have a neutral charge.

The particular amount of pharmaceutically active ingredient which can be loaded in the device of the present invention depends, inter alia, on the molecular weights and solubilities of the rigid and flexible polymers, as well as that of the pharmaceutically active ingredient. However, generally, the amount of pharmaceutically active ingredient which can be loaded in the device of the present invention is about 0.0001% (w/v) to about 1.0% (w/v) of the matrix. Preferably, the amount of drug loaded in the matrix is about 0.1% (w/v) to about 1.0% (w/v). The minimum amount of drug loaded in the matrix depends on the specific drug, and its efficacy relating to dosage amount. However, loading more than 1.0% (w/v) of the drug in the matrix can detrimentally affect the sustained release of the drug by the matrix.

The combination of rigid and flexible polymers in a single phase in the present invention gives the following unique benefits in controlling the release of pharmaceutically active ingredient over rigid polymer-only or flexible polymer-only matrices:

i. It gives a smaller overall mesh size due to its ability to fill in larger interstices that would be present in a rigid polymer-only matrix;

ii. It more effectively inhibits diffusion of the drug than a flexible polymer-only matrix due to the increased rigidity of the mixed matrix.

iii. In contrast to a cross-linked flexible polymer-only matrix or a cross-linked rigid polymer-only matrix, the mixed matrix is easily injected into a subject.

Moreover, due to the attenuated physical structure of the rigid polymer, and its interaction with the flexible polymer, the combined rigid/flexible polymer matrix is unexpectedly more effective at sustaining the release duration of pharmaceutically active ingredients having a size of 4 nm or more, particularly ones having a size of 5 nm or more, than devices composed of either polymer alone. The use of a rigid polymer also makes the flexible polymer more rigid, and provided an unexpectedly higher degree of diffusional hindrance, while also allowing the matrix to have smaller pore sizes due to the presence of the flexible polymer. The unexpectedly superior results provided by the presently claimed matrix are illustrated in the Examples and attached Figures, where a matrix of a rigid polymer and flexible polymer is compared to either a matrix of a rigid polymer alone or a matrix of a flexible polymer alone.

In addition, the non-crosslinked matrix of the present invention can be easily injected via a syringe and needle into a subject intraperitoneally or subcutaneously, and is naturally reabsorbed by the subject. The crosslinked matrix of the present invention may be in the form of a membrane, and is surgically implantable.

The following examples are provided for illustrative purposes only, and are in no way intended to limit the scope of the present invention.

EXAMPLE 1

Preparation of the Polymers

A. Rigid Polymers

Collagen was negatively-charged by succinylating vitrogen following the procedure described in U.S. Pat. No. 4,164,559, which is again incorporated herein by reference in its entirety.

Five grams of collagen was solubilized in 2.0 liters of acidified water (pH 3.0 HCl) and the pH was adjusted to 9.0 by the addition of NaOH. Acetone solution (100 ml) containing 2.0 g of succinic anhydride was then gradually added to the collagen suspension. During the addition of succinic anhydride, the pH of the the collagen suspension was maintained at about 9.0 by the addition of NaOH.

The resulting succinylated collagen was concentrated by precipitation at an acidic pH of 4.5, and centrifuged at 15,000×g at 20° C. The solvent containing acetone and water was replaced by phosphate buffered saline comprising 20 mM sodium phosphate and 130 mM sodium chloride (pH 7.0) (hereinafter, "PBS") by exhaustive dialysis. The concentration of the succinylated collagen was assayed by biuret.

B. Flexible Polymers

Hyaluronic acid polymer was purchased commercially (SIGMA CHEMICAL CORP.), and prepared by dissolving the desired amount in PBS. This polymer was characterized by gel permeation chromatography, and was shown to have a broad molecular weight distribution with an average molecular weight well over 1,000 KDa.

Different molecular weight fractions (250 KDa and 750 KDa) of polyacrylic acid polymers were also purchased commercially (Polysciences). The average molecular weights of the polymers were characterized by gel permeation chromatography.

EXAMPLE 2

Single Phase Matrix Preparation

In order to prevent bacterial contamination, preparation of single phase matrices was performed under clean conditions in a laminar flow hood.

Single phase matrices were prepared by syringe-to-syringe exchange of pre-measured volumes of the polymer solutions at 20° C. The single phase matrices prepared ranged from those containing succinylated collagen only (at a concentration of 40 mg/ml) to hyaluronic acid only (at a concentration of 30 mg/ml), as well as mixtures thereof (at a concentration of 40 mg/ml).

In the electron spin resonance studies described in Example 3 below, 1000 $\mu$l of a 1.0 mg/ml solution of TEMPO-labelled polyacrylic acid (PAA) (250 KDa and 750 KDa) were mixed and homogenized into 0.90 ml of the matrix by syringe-to-syringe exchange, to obtain a final TEMPO-labelled polyacrylic acid concentration of approximately 100 $\mu$g/ml.

In the release studies in Example 4 below, the following fluorescently-labelled biopolymers were mixed and homogenized into the matrix by syringe to syringe exchange:

(i) 200 $\mu$l of a 8.4 mg/ml solution of BSA (66 KDa) was added to 3.0 ml of matrix for a final BSA concentration of 550 $\mu$g/ml in the matrix;

(ii) 20 $\mu$l of a 9.3 mg/ml solution of anionic dextran (70 KDa) was added to 3.0 ml of matrix for a final anionic dextran concentration of 60 $\mu$g/ml in the matrix; or (iii) 75 $\mu$l of a 3.5 mg/ml solution of Ficol (400 KDa) was added to 3.0 ml of matrix for a final Ficol concentration of 85 $\mu$g/ml in the matrix.

In Example 4, the matrices typically had final matrix polymer (collagen and hyaluronic acid) concentrations of 40 mg/ml total polymer concentration in each matrix.

After mixing and homogenization, the resulting devices were allowed to equilibrate at 4° C. for 2–3 days.

EXAMPLE 3

Electron Spin Resonance Experiments

In this Example, experiments were carried out to measure the molecule architecture of the flexible polymer in the single phase matrices using Electron Spin Resonance (ESR).

The ESR studies were performed by labelling polyacrylic acid (PAA) (250 and 750 KDa) with 4-amino TEMPO (Sigma Chemical Co.; and Wielema et al, *Eur. Polym. J.*, 24: 647 (1988)). The labelling density was characterized by high pressure liquid chromatography (HPLC) to determine polymer concentration, and by ESR to determine TEMPO concentration. The label densities were found to be approximately one label per polymer molecule. Since the structure of PAA is such that there is no stearic reason for 4-amino TEMPO to prefer one labeling site to another along the polymer backbone, the labels were assumed to be randomly placed along the polymer backbone.

200 $\mu$l of viscous matrix containing the TEMPO-labelled polyacrylic acid was loaded into a TPX cover slip-quartz ESR cell typically used for analyzing tissue slices (Wilmad Corp. Piscataway, N.J.). The cell was placed in the cavity of a Varian E-4 ESR spectrometer and nitrogen was passed over the cell. Derivative ESR spectra (microwave energy absorbed versus magnetic field strength) were recorded over magnetic field strengths ranging from 3300–3400 gauss. The modulation amplitude used was 1.0 gauss, the modulation frequency was 100 KHz, the microwave power was 5.0 mW, the microwave frequency was 9.5 GHz. ESR spectra were recorded at room temperature, which was approximately 298 K.

Rotational correlation times (RCTs) were computed from the measured ESR spectra based on standard formulas (Wielema et al, *Eur. Polym. J.*, 24: 647 (1988)). The computed RCTs reflect the mobility of the TEMPO-labelled polyacrylic acid monomer units, and can be thought of as the time required for the nitroxide to undergo thermally-driven rotation of 1 radian about its principle axis. Smaller RCTs reflect faster motion (more mobility) and larger RCTs reflect slower motion (less mobility).

Figure 1:
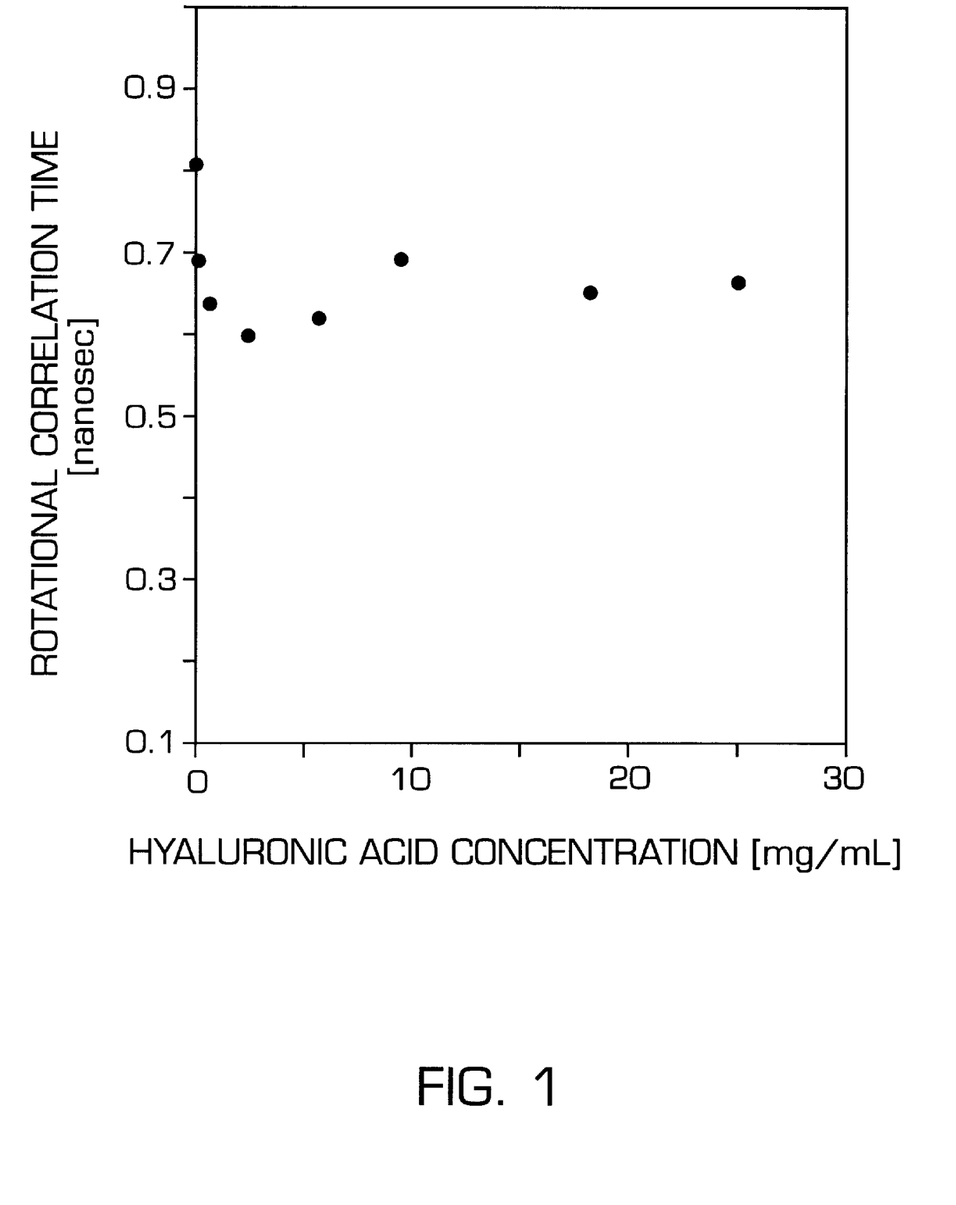
FIG. 1 shows a plot of the rotational correlation times (RCT) of a 250 KDa polyacrylic acid polymer in greater than 1,000 KDa hyaluronic acid polymer matrices as a function of the concentration of the greater than 1,000 KDa hyaluronic acid polymer in the matrices.

FIG. 1 shows a plot of the RCT of a 250 KDa polyacrylic acid polymer in greater than 1,000 KDa hyaluronic acid polymer matrices as a function of the concentration of the greater than 1,000 KDa hyaluronic acid polymer in the matrices.

Figure 2:
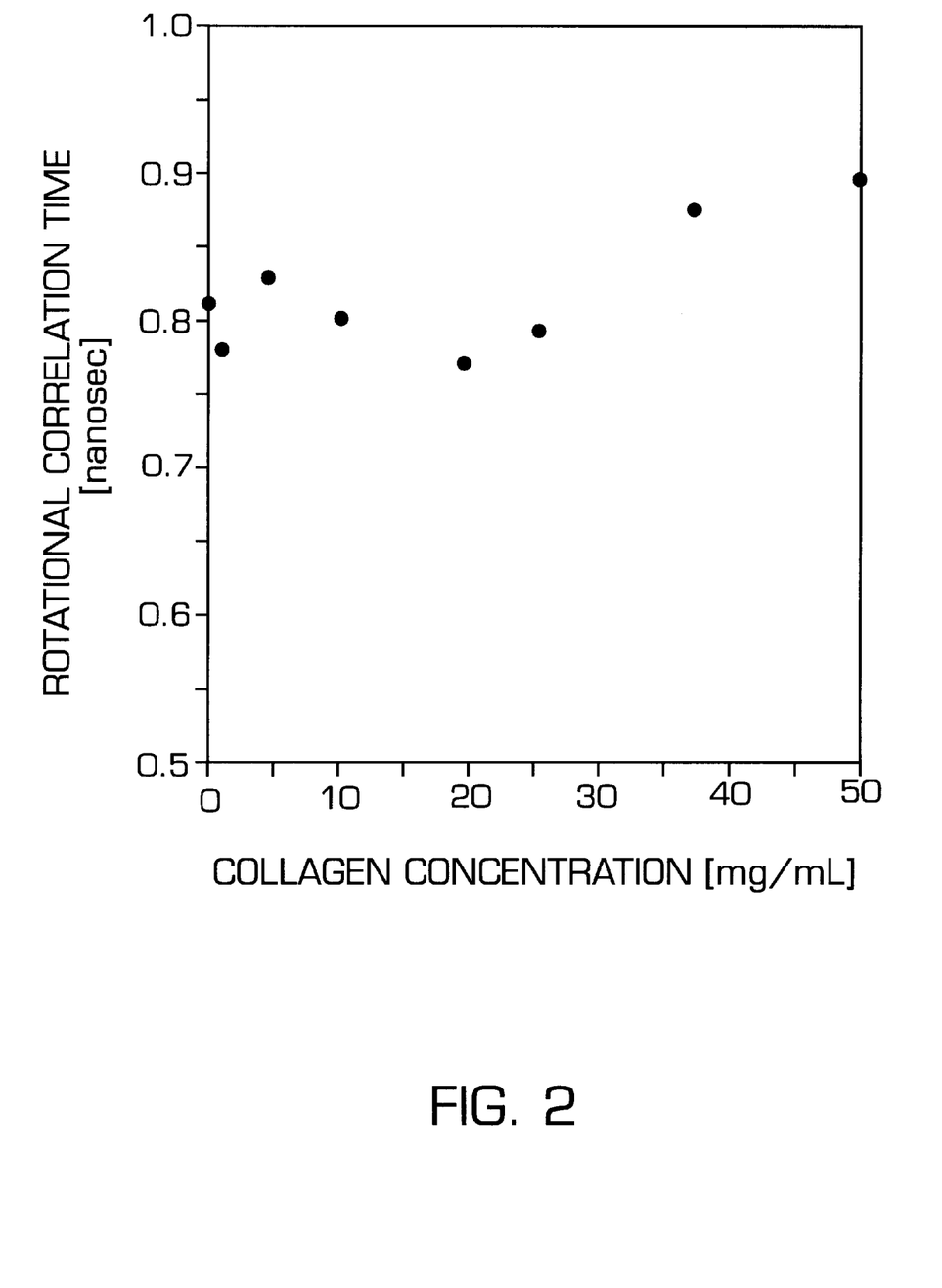
FIG. 2 shows a plot of the RCT for a 250 KDa polyacrylic acid polymer in 300 KDa succinylated collagen matrices as a function of the concentration of the 300 KDa succinylated collagen in the matrices.

FIG. 2 shows a plot of the RCT for a 250 KDa polyacrylic acid polymer in 300 KDa succinylated collagen matrices as a function of the concentration of the 300 KDa succinylated collagen in the matrices.

Figure 3:
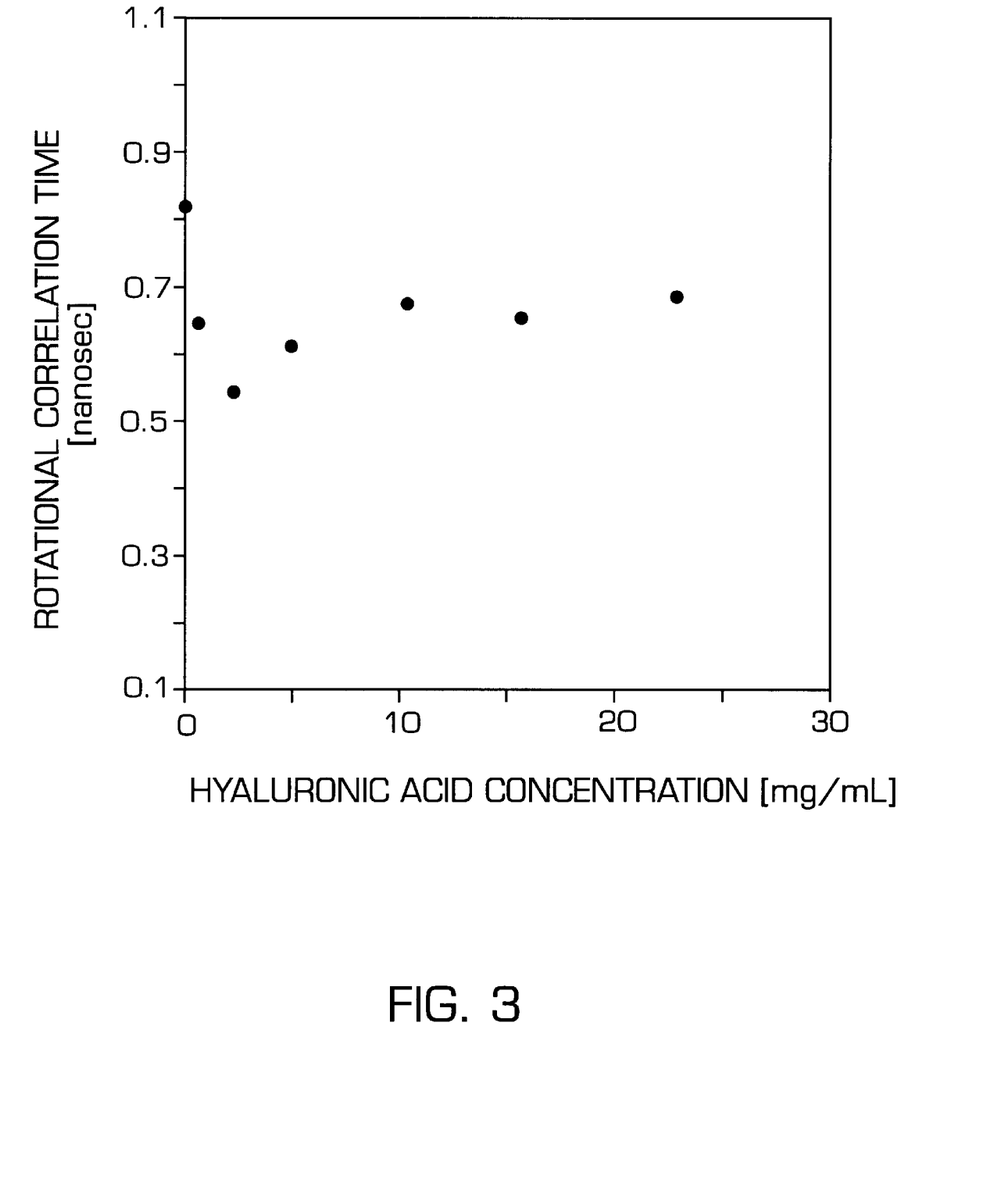
FIG. 3 shows a plot of the RCT for a 750 KDa polyacrylic acid polymer in greater than 1,000 KDa hyaluronic acid polymer matrices as a function of the concentration of the greater than 1,000 KDa hyaluronic acid polymer in the matrices.

FIG. 3 shows a plot of the RCT for a 750 KDa polyacrylic acid polymer in greater than 1,000 KDa hyaluronic acid polymer matrices as a function of the concentration of the greater than 1,000 KDa hyaluronic acid polymer in the matrices.

Figure 4:
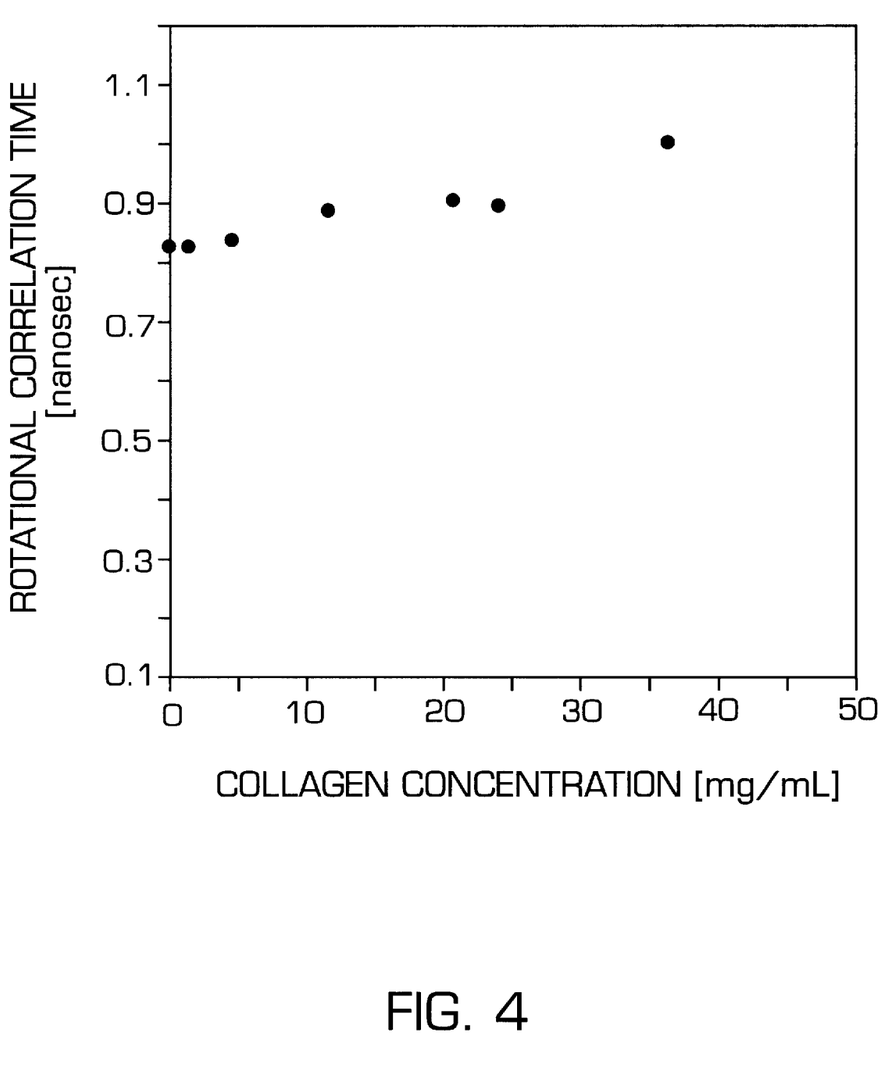
FIG. 4 shows a plot for a 750 KDa polyacrylic acid polymer in 300 KDa succinylated collagen matrices as a function of the concentration of the 300 KDa succinylated collagen in the matrices.

FIG. 4 shows a plot for a 750 KDa polyacrylic acid polymer in 300 KDa succinylated collagen matrices as a function of the concentration of the 300 KDa succinylated collagen in the matrices.

FIGS. 1–4 clearly demonstrate that the flexible polyacrylic acid behaves very differently, and assumes a special geometric configuration, when combined in a matrix with a rigid rod polymer (succinylated collagen) than when combined in a matrix with another flexible polymer (hyaluronic acid). That is, the rigid rod matrix has the effect of constraining the mobility of the flexible coil much the same way cross-linking would, but does not have the disadvantage of difficulty of in vivo administration as typically seen with cross-linked flexible polymers.

In summary, the results in FIGS. 1–4 (for both 250 KDa and 750 KDa polyacrylic acid polymers (PPA)) show that a vast difference exists between the behavior of PAA (a flexible polymer) in a rigid polymer (collagen) matrix than in a flexible polymer (hyaluronic acid) matrix. In the flexible matrix, the PAA appears to contract as the HA concentration increases (as evidenced by a smaller RCT-faster rotation) until it reaches a minimum diameter where it appears to attain a rigid-sphere limiting behavior, i.e., increasing the HA concentration beyond this limit does not further alter the molecular conformation of the PAA.

In contrast, in a collagen matrix, rather than contracting into a rigid sphere, the collagen penetrates the PAA coil and is able to slow down the local motion within the PAA coil. This interpenetration becomes progressively larger as the collagen concentration progressively increases.

These results illustrate the special architecture present in a rigid rod and flexible coil matrix. Because of the ability of the rigid rods to interpenetrate the flexible coils, the flexible coils are able to fill in the pores between the rigid rod molecules. In turn, the rigid rod molecules impede the local mobility of the flexible coil molecules, i.e., make the flexible coil molecules more rigid. These unique and unexpected results illustrate why the single phase mixture of rigid rod molecule and flexible coil molecule allow for the superior sustained release of drugs.

EXAMPLE 4

Release Rate Experiments

In this Example, experiments were carried out to compare the release rate of three different fluorescently-labelled biopolymers from matrices composed of succinylated collagen alone, a flexible polymer alone, and a single phase mixture of thereof. The matrices contained labelled-biopolymers (BSA, anionic dextran, and Ficol) in the amounts discussed above. This model experiment is conventionally used to evaluate the release rates of pharmaceutically active ingredients.

BSA (66 KDa) was labelled with FITC by mixing the reagents at a slightly basic pH as described by Kawauchi et al, *J. Biochem.*, 66: 783 (1969). Unreacted FITC was removed by exhaustive dialysis against phosphate buffered saline (20 mM sodium phosphate, 130 mM sodium chloride (pH 7.0)). The stability of the FITC-labelled-BSA (66 KDa) was tested by measuring fluorescent intensity over two weeks while incubated in PBS at room temperature. The preparation were found to be very stable.

FITC-labelled anionic dextran (70 KDa) and FITC-labelled Ficol (400 KDa) were obtained from Molecular Probes, Eugene, Oreg., and were tested for stability using the same procedure as discussed above for FITC-labelled BSA. These preparations were also found to be very stable.

The concentration of the polymers in the matrices was as follows:

40 mg/ml succinylated collagen;

29 mg/ml succinylated collagen+9.0 mg/ml hyaluronic acid;

25 mg/ml succinylated collagen+14 mg/ml hyaluronic acid;

21 mg/ml succinylated collagen+17 mg/ml hyaluronic acid;

20 mg/ml succinylated collagen+20 mg/ml hyaluronic acid;

15 mg/ml succinylated collagen+15 mg/ml hyaluronic acid; and 30 mg/ml hyaluronic acid.

Hyaluronic acid has a strong swelling tendency such that 30 mg/ml was the maximum hyaluronic acid concentration attainable, i.e., more concentrated hyaluronic acid matrices would swell absorb water from the eluting buffer.

Release rates of the above fluorescently-labelled model biopolymers were measured by pelleting the labelled-biopolymer containing matrix (the matrix volumes were 1.0 ml) in a 1.0 cm diameter flat-bottom tube through gentle centrifugation. Care was taken to remove all trapped air bubbles and to obtain a flat interface. After sufficient time (2 days) for equilibration at 22° C., 0.5 ml of eluting buffer (PBS) was carefully pipetted on top of each matrix so as not to disturb the flat interface. The eluting buffer was periodically removed, and assayed for the concentration of released model drug. The concentration of released model drug present in each sample of eluting buffer was assayed by a fluorometer. 0.5 ml of fresh eluting buffer was then placed above each matrix, and the diffusion procedure repeated. The experiments were performed at room temperature; variation in diffusion due to fluctuation in temperature, i.e., between 310 K. and 298 K., was negligible. Measurements for each matrix composition were performed in triplicate to ensure reproducibility (which was very good in all cases).

The results were analyzed by plotting the log of the amount of labelled-biopolymer loaded which was released or remaining versus time to ensure that diffusion was the dominant release mechanisms. Devices whose release profiles were not linear when plotted in this manner were rejected because binding interactions were occurring in addition to diffusional hindrance.

Figure 5:
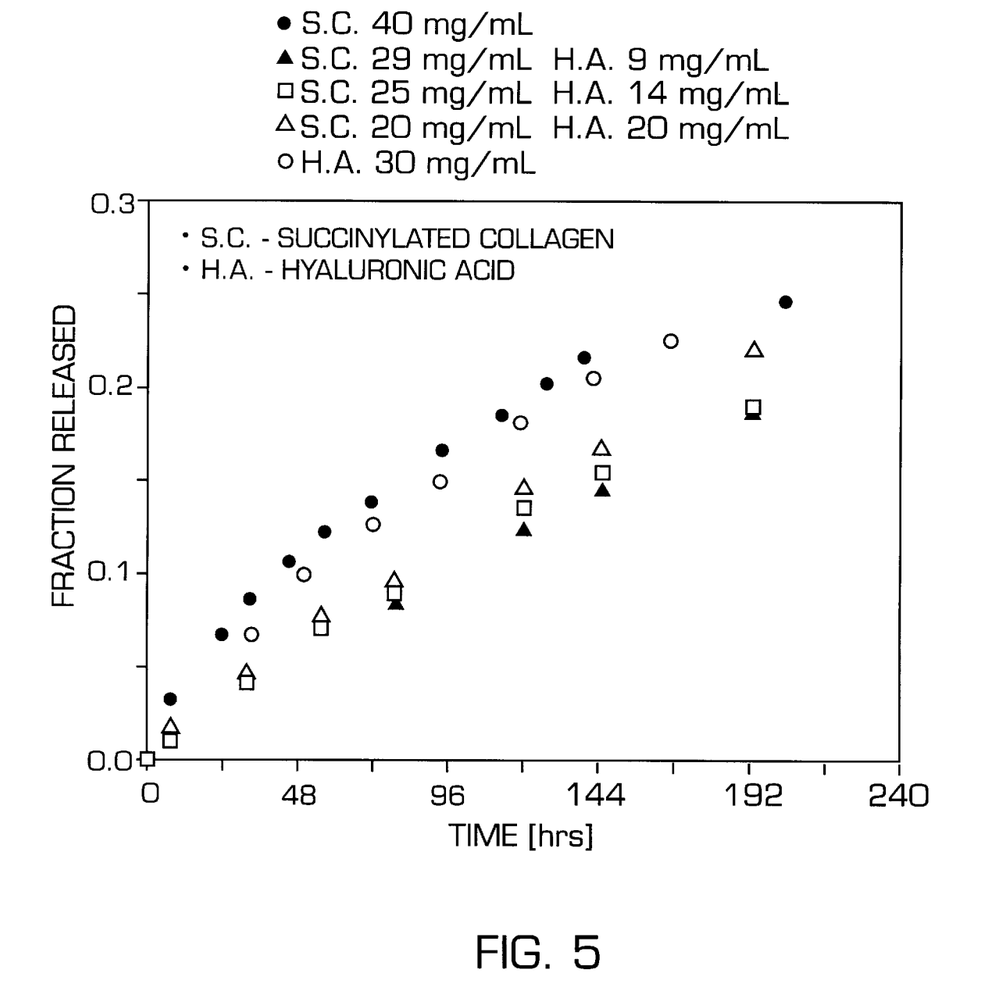
FIG. 5 shows a plot of the release rates of fluorescein isothiocyanate (FITC)-labelled anionic dextran (70 KDa) measured in five different matrices comprising 300 KDa succinylated collagen and greater than 1,000 KDa hyaluronic acid polymer. The data points represent averages of measurements performed in triplicate.

FIG. 5 shows a plot of the release rates of FITC-labelled anionic dextran (70 KDa) measured in five different matrices comprising 300 KDa succinylated collagen and greater than 1,000 KDa hyaluronic acid polymer. The slight scatter in the data reflects the limits of experimental uncertainty.

As shown in FIG. 5, the succinylated collagen-only and hyaluronic acid-only matrices gave similar release profiles (the hyaluronic acid-only matrix had a slightly slower release time). On the other hand, the release rate was significantly slower (more than 20%) in the mixed matrices.

In addition, there was a small effect on the release rates caused by the ratio of hyaluronic acid to succinylated collagen in the mixed matrices, with higher hyaluronic acid contents giving slightly faster release. The above-described effect is presumably due to an optimum point between the effects of mesh size and rigidity in these matrices. It is important to note that dextran is much more flexible than the other biopolymers (BSA and Ficol) released in this test. In the presence of hyaluronic acid, dextran will contract into a rigid sphere. However, with collagen present, the dextran never becomes rigid because the collagen is always rigid enough to penetrate the dextran coils. This result is most likely attributable to the flexibility of the drug being released. Thus, not only is the rigidity of the matrix important, but also the rigidity of the drug, in providing an optimum ratio of rigid polymer/flexible polymer in the matrix. Thus, more rigid drugs than dextran may have a slightly different optimum ratio of rigid polymer/flexible polymer in the matrix.

Figure 6:
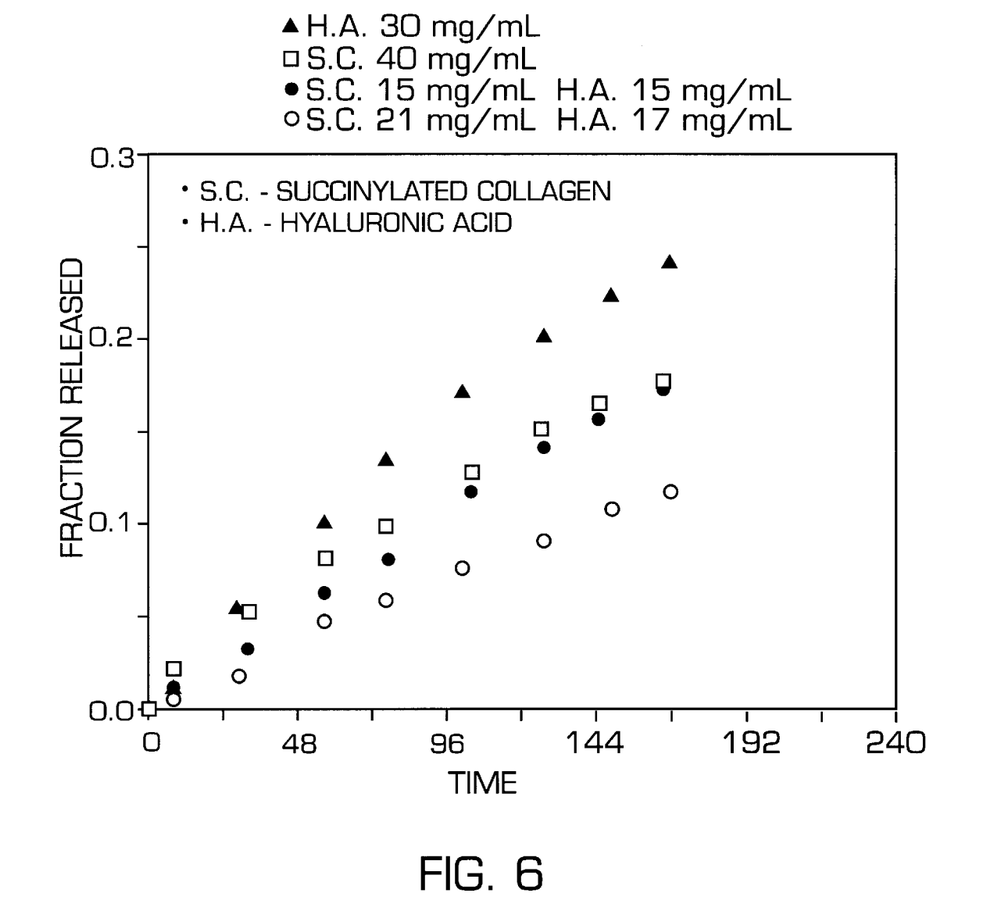
FIG. 6 shows a plot of the release rates for FITC-labelled Ficol (400 KDa) measured in four different matrices comprising 300 KDa succinylated collagen and greater than 1,000 KDa hyaluronic acid polymer. The data points represent averages of measurements performed in triplicate.

FIG. 6 shows a plot of the release rates for FITC-labelled Ficol (400 KDa) measured in four different matrices comprising 300 KDa succinylated collagen and greater than 1,000 KDa hyaluronic acid polymer. Again, the slight scatter in the data reflects the limits of experimental uncertainty.

The data in FIG. 6 for mixtures are at ratios near 50%. One mixture (30 mg/ml total polymer concentration), allows for comparison with the hyaluronic acid-only matrix. The other mixture (38 mg/ml total polymer concentration) allows for comparison with the succinylated collagen-only matrix.

Ficol is a rigid cross-linked polysaccharide. Hence, the flexibility and size of the matrix mesh are dominant. The slower release effects of the mixed matrices compared to the matrices containing only hyaluronic acid seen in FIG. 6 are more dramatic than that for the flexible biopolymer shown in FIG. 5.

Figure 7:
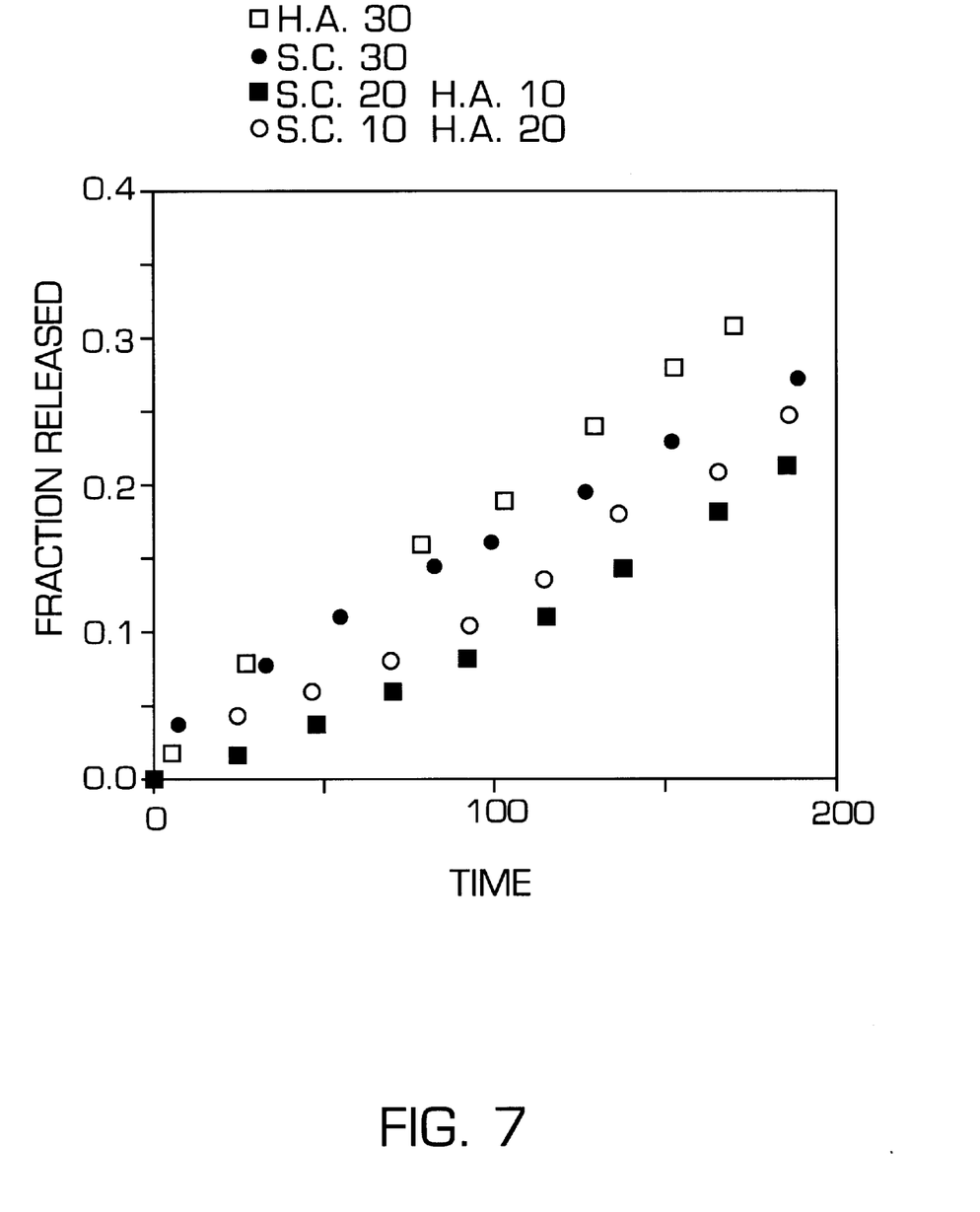
FIG. 7 shows a plot of release rates for FITC-labelled bovine serum albumin (BSA) measured in four different matrices comprising 300 KDa succinylated collagen and greater than 1,000 KDa hyaluronic acid polymer. The data points represent averages of measurements performed in triplicate.

FIG. 7 shows a plot of release rates for FITC-labelled BSA measured in four different matrices comprising 300 KDa succinylated collagen and greater than 1,000 KDa hyaluronic acid polymer.

The BSA data in FIG. 7 is all for matrices having a 30 mg/ml total polymer concentration. The BSA results are similar to the Ficol results (BSA is also much more rigid than dextran). The optimum mixture ratio appears to favor more collagen than hyaluronic acid in the mixture.

The results of FIGS. 5, 6 and 7 clearly demonstrate that release is slower for both rigid as well as flexible model drugs in the mixed rigid rod and flexible coil matrices relative to rigid rod-only or flexible coil-only matrices. These results confirm that a single phase matrix of a rigid and flexible polymer has superior drug delivery capability over a matrix having only a rigid or flexible polymer alone.

While the present invention has been described in detail above based on the specific embodiments thereof, it will be apparent to one skilled in the art that various changes and modifications can be made without departing from the spirit and the scope of the present invention.

What is claimed is:

1. A drug delivery device consisting essentially of an injectable single phase matrix solution of a negatively-charged first polymer and a negatively-charged second polymer, wherein the persistence length of the first polymer is at least 10 times the persistence length of the second polymer, wherein said negatively-charged first polymer comprises water-soluble collagen which is not cross-linked, wherein the weight ratio of said first polymer to said second polymer in said matrix is 50% to 90%, and wherein said matrix solution has dispersed therein a pharmaceutically active ingredient.

2. The drug delivery device of claim 1, wherein said first polymer is succinylated collagen.

3. The drug delivery device of claim 2, wherein said second polymer is selected from the group consisting of hyaluronic acid and polyacrylic acid.

4. The drug delivery device of claim 3, wherein said second polymer is hyaluronic acid.

5. The drug delivery device of claim 1, wherein said pharmaceutically active ingredient is selected from the group consisting of Factor VIII, Factor IX, and Protein C.

6. The drug delivery device of claim 1, wherein said first polymer has a molecular weight of from about 100 to about 1,000 KDa.

7. The drug delivery device of claim 6, wherein said first polymer has a molecular weight of from about 300 to about 600 KDa.

8. The drug delivery device of claim 1, wherein said second polymer has a molecular weight of about 100 to about 10,000 KDa.

9. The drug delivery device of claim 8, wherein said second polymer has a molecular weight of about 1,000 to about 10,000 KDa.

10. The drug delivery device of claim 1, wherein the weight ratio of said first polymer to said second polymer in said matrix is 75%.

11. The drug delivery device of claim 1, wherein said pharmaceutically active ingredient is present in amount of about 0.0001% (w/v) to about 1.0% (w/v) of the matrix.

12. The drug delivery device of claim 11, wherein said pharmaceutically active ingredient is present in amount of about 0.1% (w/v) to about 1.0% (w/v) of the matrix.

13. The drug delivery device of claim 1, wherein said pharmaceutically active ingredient is about 4 nm to about 30 nm in size.

14. The drug delivery device of claim 13, wherein said pharmaceutically active ingredient, is about 5 nm to about 20 nm in size.

15. The drug delivery device of claim 1, wherein the weight ratio of the said first polymer to said second polymer in said matrix is about 60% to 80%.

16. A method for sustained release of a pharmaceutically active ingredient in a subject, comprising:
    injecting into a subject a drug delivery device consisting essentially of an injectable single phase matrix solution of a negatively-charged first polymer and a negatively-charged second polymer, wherein the persistence length of the first polymer is at least 10 times the persistence length of the second polymer, wherein said negatively-charged first polymer comprises water-soluble collagen which is not cross-linked, wherein the weight ratio of said first polymer to said second polymer in said matrix is 50% to 90%, and wherein said matrix solution has dispersed therein a pharmaceutically active ingredient.

17. The method of claim 16, wherein said first polymer is succinylated collagen.

18. The method of claim 16, wherein said second polymer is selected from the group consisting of hyaluronic acid and polyacrylic acid.

19. The method of claim 18, wherein said second polymer is hyaluronic acid.

20. The method of claim 16, wherein said pharmaceutically active ingredient is selected from the group consisting of Factor VIII, Factor IX and Protein C.

21. The method of claim 16, wherein said first polymer has a molecular weight of from about 100 to about 1,000 KDa.

22. The method claim 21, wherein said first polymer has a molecular weight of from about 300 to about 600 KDa.

23. The method of claim 16, wherein said second polymer has a molecular weight of about 100 to about 10,000 KDa.

24. The method of claim 23, wherein said second polymer has a molecular weight of about 1,000 to about 10,000 KDa.

25. The method of claim 16, wherein the weight ratio of said first polymer to said second polymer in said matrix is about 60% to 80%.

26. The method of claim 16, wherein the weight ratio of said first polymer to said second polymer in said matrix is 75%.

27. The method of claim 16, wherein said pharmaceutically active ingredient is present in amount of about 0.0001% (w/v) to about 1.0% (w/v) of the matrix.

28. The method of claim 27, wherein said pharmaceutically active ingredient is present in the amount of about 0.1% (w/v) to about 1.0% (w/v) of the matrix.

29. The method of claim 16, wherein said pharmaceutically active ingredient is about 4 nm to about 30 nm in size.

30. The method of claim 29, wherein said pharmaceutically active ingredient is about 5 nm to about 20 nm in size.

* * * * *

UNITED STATES PATENT AND TRADEMARK OFFICE
CERTIFICATE OF CORRECTION

PATENT NO. : 5,928,667
DATED : July 27, 1999
INVENTOR(S) : Joel ROSENBLATT, Vivek SHENOY It is certified that error appears in the above-identified patent and that said Letters Patent is hereby corrected as shown below:

On the Cover Page, in the [73] Assignee: section, change "University of Maryland, Baltimore, Md." to
-- University of Maryland, Baltimore County, Baltimore, Md. --.

Signed and Sealed this

Fifteenth Day of August, 2000

Attest:

Attesting Officer

Q. TODD DICKINSON

Director of Patents and Trademarks